United States Patent
Plummer et al.

(10) Patent No.: US 10,022,458 B2
(45) Date of Patent: Jul. 17, 2018

(54) ANIMAL MODEL PROTOCOL, DIAGNOSTIC, THERAPEUTIC AND VACCINE AGAINST DIGITAL DERMATITIS

(71) Applicant: IOWA STATE UNIVERSITY RESEARCH FOUNDATION, INC., Ames, IA (US)

(72) Inventors: Paul Joseph Plummer, Boone, IA (US); Adam Krull, Ames, IA (US); Jan Shearer, Ames, IA (US); Patrick Gorden, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/062,729

(22) Filed: Mar. 7, 2016

(65) Prior Publication Data

US 2016/0256575 A1  Sep. 8, 2016

Related U.S. Application Data

(60) Provisional application No. 62/128,674, filed on Mar. 5, 2015.

(51) Int. Cl.
| | | |
|---|---|---|
| A61K 39/00 | (2006.01) | |
| A61K 39/02 | (2006.01) | |
| A61K 49/00 | (2006.01) | |
| C12N 1/20 | (2006.01) | |
| C12R 1/01 | (2006.01) | |

(52) U.S. Cl.
CPC ............ *A61K 49/0008* (2013.01); *C12N 1/20* (2013.01); *C12R 1/01* (2013.01); *A01K 2207/12* (2013.01); *A01K 2227/101* (2013.01); *A01K 2267/0337* (2013.01)

(58) Field of Classification Search
CPC ................................ A61K 39/00; A61K 39/02
USPC ........................................ 424/9.1, 9.2, 234.1
See application file for complete search history.

(56) References Cited

U.S. PATENT DOCUMENTS

| | | | |
|---|---|---|---|
| 5,096,323 A | 3/1992 | Walker et al. | |
| 6,162,429 A | 12/2000 | Wallis et al. | |
| 6,241,992 B1 | 6/2001 | Morck et al. | |
| 6,287,575 B1 | 9/2001 | Walker et al. | |
| 6,667,040 B2 | 12/2003 | Morck et al. | |
| 8,703,432 B2 | 4/2014 | Rosander et al. | |
| 2005/0129680 A1* | 6/2005 | Wentworth | ........ A61K 41/0057 424/141.1 |
| 2010/0068214 A1* | 3/2010 | Rood | ............... G01N 33/56911 424/164.1 |
| 2010/0086489 A1 | 4/2010 | Tomimori et al. | |
| 2012/0251578 A1 | 10/2012 | Lefler | |

OTHER PUBLICATIONS

Dairyforums.com—America's Online Dairy Community, "Warts and Lameness", (2014), 3 pages, last accessed on Oct. 21, 2014.
Gomez, A., et al., "An experimental infection model to induce digital dermatitis infection in cattle", Journal of Dairy Science, (2012), vol. 95, No. 4, pp. 1821-1830.
Hygieia Biological Laboratories, "Papillomatous Digital Dermatitis (PDD) and *Serpens* Species Bacterin", (2014), 2 pages, last accessed on Oct. 21, 2014.
Email from Paul Plummer to William Miller, (2014), 4 pages.
Yano, Takahisa, et al., "Identification of candidate pathogens of papillomatous digital dermatitis in dairy cattle from quantitative 16S rRNA clonal analysis", Veterinary Microbiology, (2010), vol. 143, pp. 352-362.
Zinpro Performance Materials, "Effects of DD Premix Formula Containing Zinpro Performance Minerals on the Prevention of Digital Dermatitis", Technical Bulletin,(2013), 7 pages.

* cited by examiner

*Primary Examiner* — Rodney P Swartz
(74) *Attorney, Agent, or Firm* — McKee, Voorhees & Sease, PLC

(57) ABSTRACT

Applicants have discovered a novel induction method for inducing digital dermatitis lesions consistent with the natural disease process. Applicants have prepared a consortium including a macerated tissue culture that may be used in the method as well as a novel inoculation procedure. The consortia of microbes includes isolates of *Treponema phagedenis, Porphorymonas,* and *Bacteroides* and the invention includes use of these novel isolates in preventing and treating digital dermatitis. The invention can be used to screen, test or compare the relative efficacy of various drugs and biologics for use in treatment or control of digital dermatitis.

20 Claims, No Drawings

ANIMAL MODEL PROTOCOL, DIAGNOSTIC, THERAPEUTIC AND VACCINE AGAINST DIGITAL DERMATITIS

FIELD OF THE INVENTION

The present invention relates to methods, animal models and compositions useful for the treatment and prevention of digital dermatitis. The invention includes a consortium of microbial isolates from animals with digital dermatitis and an induction protocol which reliably produces digital dermatitis for a predictable animal model thereof. The invention also includes the use of these organisms and proteins and/or fragments and derivatives thereof, isolation of immunogenic proteins therefrom and antibodies raised against the same for use in vaccines and diagnostic methods.

BACKGROUND OF THE INVENTION

Digital dermatitis (DD) is an economically important polymicrobial disease process of dairy cattle that, remains etiologically undefined. It is the leading cause of lameness in dairy cattle in the United States of America. In addition to the cost associated with treatment and lost production, DD represents a significant welfare concern for the industry.

In countries where DD is widespread, footbaths containing antibiotics are often used. These footbaths rapidly become contaminated with feces and dirt and hence function as large selective cultures of antibiotic resistant bacteria. In Sweden tetracyclines are used, but only for topical treatment of individual animals since on herd level footbaths with copper sulphate are recommended.

To date no commercial vaccine or serologic test for DD is available. Although the disease is responsive to antibiotics, a definitive bacterial cause has not been identified. Many bacteria of different genera, such as *Treponema, Fusobacterium, Dichelobacter, Prevotella*, and *Porphyromonas* have been isolated from DD lesions. *Treponema* spp. are regularly isolated from DD lesions, however attempts to induce classic disease lesions with pure culture of these microorganisms remain universally unsuccessful.

Several phylotypes of *Treponema* can be present in the same lesion. Different phylotypes have been isolated from the same animal and by cloning and sequencing of 16S rRNA genes, five different phylotypes were identified in a pooled sample from four cows. It has also been demonstrated by fluorescence in situ hybridization on biopsies from DD lesions that the distribution in the dermal layers differs between phylotypes.

In addition to the numerous phylotypes of *Treponema* within even a single lesion, and the lack of efficacy of *Treponema* based vaccines, it is widely believed that the disease is polybacterial in nature. The identity of microorganisms that work in concert with *Treponema* spp. to cause the clinical presentation of DD in cattle has remained unknown. Lack of this knowledge is an important problem because it prevents the development of effective intervention strategies that target the causative agents of DD. One important tool for studying this disease process is the development of a consistent model of disease induction that results in lesions characteristic of the naturally occurring lesions. Such a model will allow for in-depth study of the disease pathogenesis, experimental studies to try and fulfill identification of causative organisms and most importantly a model useful for testing experimental interventions. Identity of the causative organisms allows for the development of vaccines, treatments, and preventative agents.

As can be seen a need exists in the art for animal models, identification of causative agents and development of vaccines, treatments and preventative agents.

SUMMARY OF THE INVENTION

Applicants have discovered a novel induction method useful for inducing digital dermatitis lesions that appear consistent with the natural disease process. Furthermore, this method results in reasonably quick induction in the characteristic site of lesion development. This is in contrast to previous induction methods which either do not provide consistent results or induce lesions that are not consistent with natural disease. Applicants have prepared a novel microbial consortiumisolate from dermatitis lesions that may be used in the method as well as a novel inoculation procedure.

Thus one aspect of the invention includes an animal model useful for evaluating the effectiveness of possible preventatives or cures for bovine digital dermatitis comprising a bovine which has been administered the microbial consortium of the invention, especially in conjunction with lesion inducement protocol of the invention.

The protocol does not require water maceration, while previous methods required up to 18 days of a lengthy water maceration procedure involving filling wrapped feet with water every 12 hours. The method results in more rapid induction with 77-100% of sites showing lesions by day 22. Lesions that are formed are mostly in the interdigital space, the normal site of digital dermatitis infections, and finally the protocol can be used on calves as well as all ages, however use of calves can reduce costs of purchase, feeding costs and decrease the odds of confounding immunity.

The consortia of microbes includes isolates of *Treponoma* spp, *Porphorymonas*, and *Baceteroides*. The consortia also includes *Dichelobacter nodosus* and *Campylobacter ureolyticus*. This is a unique collection for use in vaccine development and progression to an induction methodology that uses a consortia of pure growth organisms isolated from DD tissue or macerated tissue itself.

The present invention aims at providing efficient methods for diagnosis of and immuno-protection against dermatitis in animals, particularly digital dermatitis in ruminants, as well as products for said purposes.

In one aspect the present invention revolves around immunogenic proteins in the microbial consortium of the invention that was isolated from digital dermatitis in cattle, and more specifically to recombinant proteins.

In a first aspect, the present invention relates to isolated *Treponema phagedenis*-like, *Porphorymonas, Baceteroides, Dichelobacter nodosus, Campylobacter ureolyticus* or other DD associated protein from the DD macerated tissue culture, to fragments and derivatives thereof capable of inducing an immune response to the same, and to fragments and derivatives capable of binding to antibodies produced by a subject in an immune response against said protein, as further defined below.

In one embodiment of the invention, the proteins, and fragments and derivatives thereof, are recombinantly produced.

In another aspect, the invention relates to nucleic acid molecules encoding the proteins, fragments and derivatives according to the invention. The invention also relates to the use of said proteins, fragments and derivatives thereof in veterinary medicine, specifically as a vaccine for prevention of digital dermatitis.

In a further aspect, the present invention provides a veterinary vaccine for protection against digital dermatitis comprising one or more of said recombinant proteins and/or active fragments thereof, and conventional and suitable adjuvants. Such a vaccine may or may not further include other *Treponema* immunogens or whole cell lysates of different *Treponema* spp. in a vaccine for a broader immune response.

According to another aspect, the present invention also relates to a method for prevention of digital dermatitis in animals comprising the step of administering said vaccine to an animal in need thereof.

According to a still further aspect, there is provided a method of detecting presence of antibodies against DD associated species present in the microbial consortia of the invention, in a sample in which said recombinant proteins and/or active fragments are used to detect the presence of antibodies against DD associated species are present.

An additional aspect of the invention is the diagnostic use of one or more isolated *Treponema*-like, *Porphorymonas, Baceteroides, Dichelobacter nodesus, Campylobacter ureolyticus* or other DD associated proteins, which in an advantageous embodiment were identified using a typical promoter sequence, which is described in detail in the Experimental part below. In one embodiment, a panel of proteins is used such as at least two, three, four or five of the above-mentioned proteins. As the skilled person will appreciate, such a panel could also include additional *Treponema* spp. proteins, not defined by sequence in this application.

Thus, according to one aspect, there is provided a method for diagnosis of digital dermatitis in an animal in which said recombinant proteins and/or active fragments are used to detect the presence of antibodies against same in an animal.

In one embodiment of said detection method or diagnostic method, said recombinant proteins and/or active fragments are used in an ELISA (Enzyme-Linked ImmunoSorbant Assay) method.

In one aspect, the present invention relates to antibodies raised against said immunogenic proteins, or immunogenic derivatives or fragments thereof. Such antibodies are useful in treatment of disease caused by *Treponema*-like, *Porphorymonas, Bacteroides, Dichelobacter nodesus, Campylobacter ureolyticus* or other DD associated proteins by way of passive immunization and also in various laboratory methods such as immunomagnetic separation of *Treponema* bacteria and others species present in the microbial consortium of the invention.

Definitions

As used herein, the following terms have the meanings ascribed to them unless specified otherwise.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

As used herein the term "*Treponema*" shall include any of the microbiological components in the consortia or macerated tissue culture disclosed and claimed herein. This can include species of *Treponema, Treponema*-like, *Porphorymonas, Bacteroides, Dichelobacter nodesus* and *Campylobacter ureolyticus* species present in said consortia, or macerated tissue culture of the invention or the DD associated proteins therefrom.

"Biological sample" refers to any sample obtained from a living or dead organism. Examples of biological samples include biological fluids and tissue specimens. Examples of tissue specimens include bovine hoof and foot tissue. Such biological samples can be prepared for analysis using in situ techniques.

A "biologically pure culture" refers to a continuous in vitro culture which is substantially free of other organisms. A culture is substantially free of other organisms if standard harvesting procedures (as described below) result in a preparation which comprises at least about 95%, preferably 99% or more of the organism, e.g., *Treponema*.

"Nucleic acids" and "polynucleotides," as used herein, may be DNA or RNA. One of skill will recognize that for use in the expression of *Treponema* proteins or as diagnostic probes, polynucleotide sequences need not be identical and may be substantially identical to sequences disclosed here. In particular, where the inserted polynucleotide sequence is transcribed and translated to produce a functional polypeptide, one of skill will recognize that because of codon degeneracy a number of polynucleotide sequences will encode the same polypeptide.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (GAP, BESTFIT, FASTA, and TFASTA in the Wisconsin Genetics Software Package, Genetics Computer Group (GCG), 575 Science Dr., Madison, Wis.), or by inspection.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences are preferably compared to a reference sequence using GAP using default parameters.

Another indication that polynucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at room temperature with a 5× saline-sodium citrate (SSC) buffer, 0.1% SDS wash.

The phrase "specifically or selectively hybridizing to," refers to hybridization between a probe and a target sequence in which the probe binds substantially only to the target sequence, forming a hybridization complex, when the target is in a heterogeneous mixture of polynucleotides and other compounds. Such hybridization is determinative of the presence of the target sequence. Although the probe may bind other unrelated sequences, at least 90%, preferably 95% or more of the hybridization complexes formed are with the target sequence.

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv, Fab, and F(ab)$_2$, as well as in single chains. Single-chain antibodies, in which genes for a heavy chain and a light chain are combined into a single coding sequence, may also be used.

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

The phrase "specifically immunoreactive with", when referring to a protein or peptide, refers to a binding reaction between the protein and an antibody which is determinative of the presence of the protein in the presence of a heterogeneous population of proteins and other compounds. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein and are described in detail below.

The phrase "substantially pure" or "isolated" when referring to a peptide or protein, means a chemical composition which is free of other subcellular components of the *Treponema* organism. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon silver staining. For certain purposes high resolution will be needed and HPLC or a similar means for purification utilized.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, dioxigenin, or haptens and proteins for which antisera or monoclonal antibodies are available.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker, or through ionic, van der Waals or hydrogen bonds to a label such that the presence of the probe may be detected by detecting the presence of the label bound to the probe. "Amplification" primers are oligonucleotides comprising either natural or analogue nucleotides that can serve as the basis for the amplification of a select nucleic acid sequence. They include, e.g., polymerase chain reaction primers and ligase chain reaction oligonucleotides.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

"Pharmaceutically acceptable" means a material that is not biologically or otherwise undesirable, i.e., the material can be administered to an individual along with a *Treponema* antigen without causing any undesirable biological effects or interacting in a deleterious manner with any of the other components of the pharmaceutical composition.

An "immunogenic agent", or "immunogen", is capable of inducing an immunological response against itself on administration to a patient, optionally in conjunction with an adjuvant.

An "active fragment" or "active derivative" as used in the present specification is a fragment or derivative of a native immunogenic agent, capable of inducing an immunological response against said native immunogenic agent on administration to a patient, optionally in conjunction with an adjuvant. An active fragment or derivative comprises or mimics at least one "epitope" or "antigenic determinant".

A "binding fragment" or "binding derivative" as used in the present specification is a fragment or derivative of a native immunogenic agent, capable of immunospecific binding to antibodies produced by a subject in an immune response against said native immunogenic agent. A binding fragment or derivative comprises or mimics at least one "epitope" or "antigenic determinant".

A "derivative" of a protein may be a protein showing substantial sequence homology to the original protein. The sequence homology may be 50% identity or more, such as 65%, 80%, 85%, 90%, 95% or 99% identity in amino acid sequence. The substituted amino acids are preferably conservative substitutions. The substituted amino acids may be natural or non-natural amino acids.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996).

Antibodies that recognize the same epitope can be identified in a simple immunoassay showing the ability of one antibody to block the binding of another antibody to a target immunogen, or fragment or derivative thereof.

The term "antibody" refers to an intact antibody, or a binding fragment thereof. An antibody may comprise a complete antibody molecule (including polyclonal, monoclonal or chimeric), or comprise an antigen binding fragment thereof. Antibody fragments include F(ab').sub.2, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136).

DETAILED DESCRIPTION OF THE INVENTION

I. Animal Models of DD

The invention includes a novel abrasion protocol to produce lesions in the feet of bovine which are then inoculated with the either the consortia or pure growth organisms or the macerated tissue of the invention. The consortia includes microorganisms isolated from animals with DD, and the other inoculant includes macerated tissue.

The consortia of pure growth organisms includes a combination of at least 7 strains, including *Treponema*-like, *Porphorymonas, Bacteroides, Dichelobacter nodesus, Camplylobacter ureolyticus*. Other strains may be identified and isolated from the macerated tissue culture of the invention (ATCC PTA-124690).

The abrading protocol does not require water maceration, while previous methods required up to 18 days of a lengthy water maceration procedure involving filling wrapped feet with water every 12 hours. The method results in more rapid induction with 77-100% of sites showing lesions by day 22. Lesions that are formed are mostly in the interdigital space, the normal site of digital dermatitis infections, and finally the protocol uses calves as opposed to dairy heifers reducing costs of purchase, feeding costs and decreasing the odds of confounding immunity. The Protocol includes the use of up to 40 Induction Calves. On the first day all 4 feet are Abraded and wrapped with a wrap soaked in sterilized rumen fluid or induction specific bacterial media. Any anaerobic growth media may be used according to the invention. One Induction Broth which may be used includes a mixture of sterile growth media that contained 40% MTGE (Anaerobe Systems, Morgan Hill, Calif.), 30% Brain Heart Infusion Broth (BD and Company, Sparks, Md.) 15% Trypticase Arginine Serine Broth (58), and 15% Mueller Hinton Broth (BD and Company, Sparks, Md.).

After 2-4 days the feet are inoculated per below:

Macerate Preparation:

The inocula is prepared using tissue lesion biopsies from adult cows with naturally occurring stage A1, A2, B1, B2, 3, and 4 digital dermatitis lesions (as described in the Iowa Digital Dermatitis scoring system. A total of up to 2 gram of lesion material per desired foot to be inoculated is harvested and placed into Induction Broth with the addition of 20% Fetal Bovine Serum (Sigma-Aldrich, St. Louis, Mo.). The lesions are combined and macerated in an anaerobic chamber using two scalpel blades. In larger preparations, lesions are collected from slaughterhouses and macerated using an industrial blender placed in an anaerobic chamber. The collected lesions are mixed with inoculation media and macerated, filtered and frozen at −80 C.

Option 1: 1.5 ml Anaerobic Enrichment Broth such as MTGE (Available from Anaerobe Systems, Inc. (an enriched non-selective medium for the cultivation and isolation of most anaerobic bacteria and other fastidious microorganisms) broth only Option 2: 1.5 ml Lesion Material (macerated tissue culture of the invention) (0.75 ml Lesion, 0.75 ml MTGE or induction specific broth)

Option 3: 0.15 mL of lesion macerate in a total of 1.5 mL of MTGE or lesion broth Option 4: 1.5 mL of Lesion Material (macerated tissue culture of the invention) frozen and stored at −80 C immediately after preparation and thawed immediately prior to induction.

II. Screening Candidate Compounds for Treatment of DD

Accordingly a further object of the present invention relates a method for screening a candidate compound for use as a drug for the treatment or prevention of DD, and/or its symptoms comprising i) administering to the animal model of the invention a candidate compound, ii) characterizing the phenotype animal model of the invention after the administration of the candidate compound and iii) positively selecting the candidate compound that reverses, delays or ameliorates the symptoms of DD.

The method of the invention is thus particularly suitable for identifying drugs for the treatment of DD and/or for identifying drugs for the treatment and prevention of the main complications of DD. The effect of the candidate compound on animal model may be evaluated by determining whether the candidate compound causes a reversal, or ameliorates in any way any of the cellular or physiological changes caused by the disease (e.g. Decrease in severity, number or total area of lesions, entire transformation of moist, red, raw, prone-to-bleed, painful surfaces to dry, dark brown, firm, rubbery, keratinacious, non-painful surfaces adherent to underlying pink healthy-appearing skin, decrease in pain associated with the lesion). Typically, the candidate compounds can be tested using the assays and tests as described in the Examples herein.

Suitable candidate compounds which may be tested in the above methods include antibody products (for example, monoclonal and polyclonal antibodies, single chain antibodies, chimeric antibodies and CDR grafted antibodies). Furthermore, combinatorial libraries, defined chemical identities, small molecules, peptides and peptide mimetics, oligonucleotides and natural product libraries, such as display libraries (e.g. phage display libraries) may also be tested.

Candidate compounds positively selected in the screening methods of the invention may be used to prevent or treat DD. Accordingly, condition of an animal patient suffering from such a disease can therefore be improved by administration of such a product. The formulation of the product for use in preventing or treating the disease will depend upon factors such as the nature of the agent identified, the precise combination of symptoms, and the severity of the disease. Typically the agent is formulated for use with a pharmaceutically acceptable carrier or diluent. For example it may be formulated for intracranial, parenteral, intravenous, intramuscular, subcutaneous, transdermal or oral administration. A veterinarian will be able to determine the required route of administration for each particular patient. The pharmaceutical carrier or diluent may be, for example, an isotonic solution. The dose of product may be determined according to various parameters, especially according to the substance used; the age, weight and condition of the patient to be treated; the route of administration; the severity of the disease, and the required regimen. A suitable dose may however be from 0.1 to 100 mg/kg body weight such as 1 to 40 mg/kg body weight. Again, a veterinarian will be able to determine the required route of administration and dosage for any particular patient.

The present invention also provides a kit for screening a candidate compound for use as a drug for the treatment or prevention of DD, which kit comprises a non-human animal model of the invention, and means for determining whether the candidate compound can ameliorate the phenotype of the animal model.

III. Preparation of DD Associated Polypeptides and Nucleic Acids

Standard protein isolation and purification techniques can be used to isolate proteins from the cultures provided here. Such techniques include standard immunoblot techniques, selective precipitation with such substances as ammonium sulfate, column chromatography, immunopurification methods, and the like (see, e.g., Scopes, Protein Purification: Principles and Practice (1982)).

Once proteins have been identified, standard protein purification methods can be used to purify these proteins and produce polyclonal or monoclonal antibodies for use in diagnostic methods described below. Such antigens are useful in enzyme-linked immunoassays (ELISA) and immunoperoxidase assays on in situ fixed tissue for the detection of *Treponema*-specific antibodies in DD infected cattle.

The present invention also relates to a method of identifying fragments of one of the proteins according to the invention, which fragments are capable of specific binding to antibodies produced by a subject in an immune response against said protein. Once aware of the proteins, the skilled person is able to perform such a method using well known routine technologies.

Screening of antigenicity of *Treponema* protein fragments according to the invention could for example be performed as follows. *Treponema* proteins are first fragmented, and the antigenicity of these fragments investigated in an array. Suitable array formats are well known to the skilled person. For example, protein specific phage display libraries are generated, e.g. as described in the experimental part below but using one specific gene for one library instead of whole genomic DNA. Such phage libraries can be selected against antibodies to identify fragments, which constitute specific epitopes. Specific PCR products, based on results from using the protein specific phage libraries, or PCR products corresponding to random fragments may be produced. The PCR products are cloned into suitable vectors for heterologous expression in e.g. *Escherichia coli*, and the protein fragment products so generated are screened for antigenicity using a suitable method, such as in 96-well plates of standard format, by adding recombinant fragments to individual wells. Sera from infected animals and from control animals are added, and the presence of host antibodies is detected by ELISA to identify a fragment according to the invention.

Rather than extract the proteins directly from cultured microbial consortia of the invention, nucleic acids derived from the cultures can be used for recombinant expression of the proteins. In these methods, the nucleic acids encoding the proteins of interest are introduced into suitable host cells, followed by induction of the cells to produce large amounts of the protein. The invention relies on routine techniques in the field of recombinant genetics, well known to those of ordinary skill in the art. A basic text disclosing the general methods of use in this invention is Sambrook et al., Molecular Cloning, A Laboratory Manual, Cold Spring Harbor Publish., Cold Spring Harbor, N.Y. 2nd ed. (1989).

Nucleic acids for use as diagnostic oligonucleotide probes or for the recombinant expression of proteins can be isolated using a number of techniques. For instance, portions of proteins isolated from the cultures discussed above can be sequenced and used to design degenerate oligonucleotide probes to screen a cDNA library. Amino acid sequencing is performed and oligonucleotide probes are synthesized according to standard techniques as described, for instance, in Sambrook et al., supra. Alternatively, oligonucleotide probes useful for identification of desired genes can also be prepared from conserved regions of related genes in other species.

Alternatively, amplification techniques such as polymerase chain reaction technology (PCR) can be used to amplify nucleic acid sequences of the desired gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of the mRNA in physiological samples, for nucleic acid sequencing, or for other purposes (for a general overview of PCR, see PCR Protocols: A Guide to Methods and Applications. (Innis et al., eds., 1990).

Standard transfection methods are used to produce prokaryotic, mammalian, yeast or insect cell lines which express large quantities of the desired polypeptide, which is then purified using standard techniques (see, e.g., Colley et al., J. Biol. Chem. 264:17619-17622, 1989; Guide to Protein Purification, supra).

The nucleotide sequences used to transfect the host cells can be modified to yield *Treponema* polypeptides with a variety of desired properties. For example, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half-life, improving therapeutic efficacy, and lessening the severity or occurrence of side effects during therapeutic use. The amino acid sequence variants are usually predetermined variants not found in nature but exhibit the same immunogenic activity as naturally occurring protein. In general, modifications of the sequences encoding the polypeptides may be readily accomplished by a variety of well-known techniques, such as site-directed mutagenesis (see Gillman & Smith, Gene 8:81-97 (1979); Roberts et al., Nature 328:731-734 (1987)). One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit a protective immune response can be easily determined using in vitro assays. For instance, the polypeptides can be tested for their ability to induce lymphoproliferation, T cell cytotoxicity, or cytokine production using standard techniques.

The particular procedure used to introduce the genetic material into the host cell for expression of the polypeptide is not particularly critical. Any of the well-known procedures for introducing foreign nucleotide sequences into host cells may be used. These include the use of calcium phosphate transfection, spheroplasts, electroporation, liposomes, microinjection, plasmid vectors, viral vectors and any of the other well-known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

Any of a number of well-known cells and cell lines can be used to express the polypeptides of the invention. For instance, prokaryotic cells such as *E. coli* can be used. Eukaryotic cells include, yeast, Chinese hamster ovary (CHO) cells, COS cells, and insect cells.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses.

The expression vector typically contains a transcription unit or expression cassette that contains all the elements required for the expression of the polypeptide DNA in the host cells. A typical expression cassette contains a promoter operably linked to the DNA sequence encoding a polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

Following the growth of the recombinant cells and expression of the polypeptide, the culture medium is harvested for purification of the secreted protein. The media are typically clarified by centrifugation or filtration to remove cells and cell debris and the proteins are concentrated by adsorption to any suitable resin or by use of ammonium sulfate fractionation, polyethylene glycol precipitation, or by ultrafiltration. Other routine means known in the art may be equally suitable. Further purification of the polypeptide can be accomplished by standard techniques, for example, affinity chromatography, ion exchange chromatography, sizing chromatography, $His_6$ tagging and Ni-agarose chromatography (as described in Dobeli et al., Mol. and Biochem. Parasit. 41:259-268 (1990)), or other protein purification techniques to obtain homogeneity. The purified proteins are then used to produce pharmaceutical compositions, as described below.

An alternative method of preparing recombinant polypeptides useful as vaccines involves the use of recombinant viruses (e.g., vaccinia). Vaccinia virus is grown in suitable cultured mammalian cells such as the HeLa S3 spinner cells, as described by Mackett et al., in DNA cloning Vol. II: A practical approach, pp. 191-211 (Glover, ed.).

IV. Antibody Production

The isolated proteins or cultures of the present invention can be used to produce antibodies specifically reactive with DD associated antigens. If isolated proteins are used, they may be recombinantly produced or isolated from the microbial consortia disclosed herein. Synthetic peptides made using the protein sequences may also be used.

Methods of production of polyclonal antibodies are known to those of skill in the art. In brief, an immunogen, preferably a purified protein, is mixed with an adjuvant and animals are immunized. When appropriately high titers of antibody to the immunogen are obtained, blood is collected from the animal and antisera is prepared. Further fractionation of the antisera to enrich for antibodies reactive to DD associated proteins can be done if desired (see Harlow & Lane, Antibodies: A Laboratory Manual (1988)).

Polyclonal antisera to the 1-9185MED and 2-1498 isolates have been produced and evaluated. The polyclonal antisera are used to identify and characterize DD associated antigens in the tissues of infected animals using, for instance, in situ techniques and immunoperoxidase test procedures described in Anderson et al. JAVMA 198:241 (1991) and Barr et al. Vet. Pathol. 28:110-116 (1991).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, Eur. J. Immunol. 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Monoclonal antibodies produced in such a manner are used, for instance, in ELISA diagnostic tests, immunoperoxidase tests, immunohistochemical tests, for the in vitro evaluation of spirochete invasion, to select candidate antigens for vaccine development, protein isolation, and for screening genomic and cDNA libraries to select appropriate gene sequences.

V. Diagnosis of DD Infections

The present invention also provides methods for detecting the presence or absence of DD in a biological sample. For instance, antibodies specifically reactive with *Treponema* or other DD associated pathogens can be detected using either DD associated proteins or the microbial isolates described here. The proteins and isolates can also be used to raise specific antibodies (either monoclonal or polyclonal) to detect the antigen in a sample. In addition, the nucleic acids disclosed and claimed here can be used to detect *Treponema*-specific sequences using standard hybridization techniques. Each of these assays is described below.

A. Immunoassays

For a review of immunological and immunoassay procedures in general, see Basic and Clinical Immunology (Stites & Terr ed., 7th ed. 1991)). The immunoassays of the present invention can be performed in any of several configurations, which are reviewed extensively in Enzyme Immunoassay (Maggio, ed., 1980); Tijssen, Laboratory Techniques in Biochemistry and Molecular Biology (1985)). For instance, the proteins and antibodies disclosed here are conveniently used in ELISA, immunoblot analysis and agglutination assays.

In brief, immunoassays to measure anti-DD antibodies or antigens can be either competitive or noncompetitive binding assays. In competitive binding assays, the sample analyte (e.g., anti-*Treponema* antibodies) competes with a labeled analyte (e.g., anti-*Treponema* monoclonal antibody) for specific binding sites on a capture agent (e.g., isolated *Treponema* protein) bound to a solid surface. The concentration of labeled analyte bound to the capture agent is inversely proportional to the amount of free analyte present in the sample.

Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means.

A number of combinations of capture agent and labelled binding agent can be used. For instance, an isolated *Treponema* protein or culture can be used as the capture agent and labelled anti-bovine antibodies specific for the constant region of bovine antibodies can be used as the labelled binding agent. Goat, sheep and other non-bovine antibodies specific for bovine immunoglobulin constant regions (e.g., γ or μ) are well known in the art. Alternatively, the anti-bovine antibodies can be the capture agent and the antigen can be labelled.

Various components of the assay, including the antigen, anti-*Treponema* antibody, or anti-bovine antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component may be covalently bound or noncovalently attached through nonspecific bonding.

Alternatively, the immunoassay may be carried out in liquid phase and a variety of separation methods may be employed to separate the bound labeled component from the unbound labelled components. These methods are known to those of skill in the art and include immunoprecipitation, column chromatography, adsorption, addition of magnetizable particles coated with a binding agent and other similar procedures.

An immunoassay may also be carried out in liquid phase without a separation procedure. Various homogeneous immunoassay methods are now being applied to immunoassays for protein analytes. In these methods, the binding of the binding agent to the analyte causes a change in the signal emitted by the label, so that binding may be measured without separating the bound from the unbound labelled component.

Western blot (immunoblot) analysis can also be used to detect the presence of antibodies to *Treponema* in the sample. This technique is a reliable method for confirming the presence of antibodies against a particular protein in the sample. The technique generally comprises separating proteins by gel electrophoresis on the basis of molecular weight, transferring the separated proteins to a suitable solid support, (such as a nitrocellulose filter, a nylon filter, or derivatized nylon filter), and incubating the sample with the separated proteins. This causes specific target antibodies present in the sample to bind their respective proteins. Target antibodies are then detected using labeled anti-bovine antibodies.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3$H, $^{125}$I, $^{35}$S, $^{14}$C, or $^{32}$P was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see U.S. Pat. No. 4,391,904, which is incorporated herein by reference.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

Some assay formats do not require the use of labelled components. For instance, agglutination assays can be used to detect the presence of the target antibodies. In this case, antigen-coated particles are agglutinated by samples comprising the target antibodies. In this format, none of the components need be labelled and the presence of the target antibody is detected by simple visual inspection.

B. Detection of *Treponema* Nucleic Acids

As noted above, this invention also embraces methods for detecting the presence of *Treponema* DNA or RNA in biological samples. These sequences can be used to detect *Treponema* in biological samples from hooved animals such as cattle. A variety of methods of specific DNA and RNA measurement using nucleic acid hybridization techniques are known to those of skill in the art (see Sambrook et al., supra).

One method for determining the presence or absence of *Treponema* DNA in a sample involves a Southern transfer. Briefly, the digested DNA is run on agarose slab gels in buffer and transferred to membranes. In a similar manner, a northern transfer may be used for the detection of *Treponema* mRNA in samples of RNA. Hybridization is carried out using labelled oligonucleotide probes which specifically hybridize to *Treponema* nucleic acids. Labels used for this purpose are generally as described for immunoassays. Visualization of the hybridized portions allows the qualitative determination of the presence or absence of *Treponema* genes.

A variety of other nucleic acid hybridization formats are known to those skilled in the art. For example, common formats include sandwich assays and competition or displacement assays. Hybridization techniques are generally described in Nucleic Acid Hybridization, A Practical Approach (Hades et al., eds. 1985); Gall & Pardue, Proc. Natl. Acad. Sci. U.S.A., 63:378-383 (1969); and Burnsteil & Jones Nature, 223:582-587 (1969). Sandwich assays are commercially useful hybridization assays for detecting or isolating nucleic acid sequences. Such assays utilize a "capture" nucleic acid covalently immobilized to a solid support and labelled "signal" nucleic acid in solution. The biological sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for detecting *Treponema* nucleic acids is in situ hybridization. In situ hybridization assays are well known and are generally described in Angerer et al., Methods Enzymol., 152:649-660 (1987). In situ hybridization assays use cells or tissue fixed to a solid support, typically a glass slide. If DNA is to be probed, the cells are denatured with heat or alkali. The cells are then contacted with a hybridization solution at a moderate temperature to permit annealing of labelled *Treponema* specific probes. The probes are preferably labelled with radioisotopes or fluorescent reporters.

Exemplary nucleic acid sequences for use in the assays described above include sequences from the 16S rRNA sequences disclosed here. For instance, primer and probe sequences derived from the 16S rRNA sequences of the isolates described herein can be used to amplify and identify nucleic acids of bovine *Treponema* in frozen or formalin-fixed foot tissue, or foot tissue fixed for in situ hybridization. Such 16S rRNA primers are particularly useful for the diagnosis of DD.

VI. Pharmaceutical Compositions

A pharmaceutical composition prepared using anti-*Treponema* monoclonal antibodies or fragments thereof as well as *Treponema* cells, proteins or their immunogenic equivalents can be used in a variety of pharmaceutical preparations for the treatment and/or prevention of *Treponema* infections. The pharmaceutical compositions are typically used to vaccinate hooved animals such as cattle, sheep, goats and other animals infected by *Treponema.*

The immunogenic whole cell organism, which is employed as the active component of the present vaccines, consists essentially of inactivated PDD-associated *Treponema* spp. These spirochetes can be isolated from animals affected with PDD, as described above. The spirochetes can be maintained in infected animals, or in suitable nutrient media. The immunogenic spirochetes are typically isolated from skin of affected animals and cultured in defined media.

Another suitable vaccine is a subunit vaccine that elicits antibody and cell-mediated immunity (CMI) to antigens of bovine *Treponema*. Experimental evidence indicates that CMI is an important component of the protective immune response in cattle. A variety of methods for evaluating the specificity of the helper and cytotoxic T cell response to selected antigens in vitro can be used.

To prepare the vaccine, the spirochetes are first separated from the medium by centrifugation or filtration, or with the use of selective media and the like. The spirochetes can be treated by a number of methods, including chemical treatment, to inactivate them. The spirochetes suspensions can be dried by lyophilization or frozen in an aqueous suspension thereof to yield inactivated whole cells.

The dried or cultured whole cells are then adjusted to an appropriate concentration, optionally combined with a suitable vaccine adjuvant, and packaged for use. Suitable adjuvants include but are not limited to: surfactants, e.g., hexadecylamine, octadecylamine, lysolectithin, dimethyldioctadecylammonium bromide, N,N-dioctadecyl-N'—N-bis(2-hydroxyethyl-propane diamine), methoxyhexadecylglycerol, and pluronic polyols; polyanions, e.g., pyran, dextran sulfate, dipeptide, dimethylglycine, tuftsin; oil emulsions; and alum. Finally, the immunogenic product can be incorporated into liposomes for use in a vaccine formulation, or may be conjugated to polysaccharides or other polymers.

The absolute weight of the deactivated whole cells varies widely, and depends upon factors such as age, weight and physical condition of the subject considered for vaccination. Such factors can be readily determined by the clinician or veterinarian employing animal models or other test systems which are all known to the art. A unit dose of the vaccine is preferably administered parenterally, e.g., by subcutaneous or by intramuscular injection.

For parenteral administration, the antigen may be combined with a suitable carrier. For example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid, *Bordetella pertussis*, and the like. Such adjuvants are available commercially from various sources, for example, Merck Adjuvant 6 (Merck and Company, Inc., Rahway, N.J.). Other suitable adjuvants are MPL+TDM Emulsion (RIBBI Immunochem Research Inc. U.S.A.). Other immuno-stimulants include interleukin 1, interleukin 2 and interferon-gamma. These proteins can be provided with the vaccine or their corresponding genetic sequence provided as a functional operon with a recombinant vaccine system such as vaccinia virus. The proportion of antigen and adjuvant can be varied over a broad range so long as both are present in effective amounts.

In addition to the *Treponema* antigen, the vaccine can also include antigens to other ungulate diseases. For example, the vaccine can include antigens to ungulate *Fusobacterium necrophorum, Porphyromonas levii*, and *Dichelobacter nodosus* (the organisms that cause interdigital necrobacillosis, commonly known as foot rot), leptospiral bacteria, bovine respiratory syncytial virus, bovine Herpes virus, bovine diarrhea virus, bovine parainfluenza virus, vesicular stomatitis virus, malignant catarrhal fever virus, blue tongue virus, pseudorabies virus, rabies virus, rinderpest virus, and Clostridia spp. antigen.

Vaccine compositions of the invention are administered to a cattle, sheep, horses, or goats susceptible to or otherwise at risk of infection to induce an immune response against the antigen and thus enhance the patient's own immune response capabilities. Such an amount is defined to be an "immunogenically effective amount." In this use, the precise amounts depend on the judgment of the vaccine manufacturer and prescribing veterinarian and would include consideration of the patient's state of health and weight, the mode of administration, the nature of the formulation, and the like. Generally, on a per-dose basis, the concentration of the *Treponema* antigen, typically the whole cell, can range from about 10 to about $10^9$ cells per ungulate patient, or 1 μg to about 100 mg antigen per ungulate patient. For administration to cattle, a preferable range is from about $10^3$ to $10^6$ cells or 100 μg to 1 mg antigen per unit dose. A suitable dose volume range is 0.5 to 2.0 ml, preferably about 2 ml. Accordingly, a typical dose for subcutaneous injection, for example, would comprise 2 ml containing $10^4$ cells or 500 μg of antigen.

A variety of vaccination regimens may be effective in immunizing cattle and other animals. For example, ungulate young and adults can both be vaccinated, preferably calves. A second immunization will be given 2-4 weeks after initial immunization. Animals that have been previously exposed to *Treponema* may require booster injections. The booster injection is preferably timed to coincide with times of maximal challenge and/or risk of abortion. Different immunization regimes may be adopted depending on the judgment of the veterinarian.

Vaccines of the invention may comprise a crude extract of *Treponema*. Chemically fixed cells can also be used. As noted above, preferred vaccines comprise partially or completely purified *Treponema* protein preparations. The antigen produced by recombinant DNA technology is preferred because it is more economical than the other sources and is more readily purified in large quantities.

In addition to use in recombinant expression systems, the isolated *Treponema* gene sequences can also be used to transform viruses that transfect host cells in animals. Live attenuated viruses, such as vaccinia or adenovirus, are convenient alternatives for vaccines because they are inexpensive to produce and are easily transported and administered.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA encoding the *Treponema* protein or fragments thereof into plasmids so that they are flanked by viral sequences on both sides. The DNA encoding *Treponema* polypeptides are then inserted into the virus genome through homologous recombination. Preferentially, a viral vaccine using recombinant vaccinia virus is used. A vaccine prepared utilizing the gene encoding the *Treponema* protein incorporated into vaccinia virus would comprise stocks of recombinant virus where the gene encoding the *Treponema* protein is integrated into the genome of the virus in a form suitable for expression of the gene.

All publications and patent applications mentioned in the specification indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

Example 1

Summary of Calf Induction Model Using Macerated Lesion Brief Protocol:

15 Induction Calves:

Day 1: Abrade all 4 feet of all calves and wrap—soak with sterilized rumen fluid Day 3: Inoculate with:
- Foot 1: 1.5 ml MTGE broth only
- Foot 2: 1.5 ml Lesion Material (0.75 ml Lesion, 0.75 ml MTGE)
- Foot 3: 1.5 ml Lesion Material+*Dichelobacter* (0.75 ml Lesion, 0.75 ml ATCC *Dichelobacter* culture* in MTGE broth)
- Foot 4: 1.5 ml Lesion Material+Trep *phagedenis* (0.75 ml Lesion, 0.75 ml 72 hour cultures of Isolates 189, 190, 191 in MTGE) (for induction one foot of each calf was induced with a randomly assigned protocol from above)

Day 5: Inoculate with:
- Foot 1: 1.5 ml MTGE broth only
- Foot 2: 1.5 ml Lesion Material (0.75 ml Lesion, 0.75 ml MTGE)
- Foot 3: 1.5 ml Lesion Material+*Dichelobacter* (0.75 ml Lesion, 0.75 ml ATCC *Dichelobacter* culture* in MTGE broth)
- Foot 4: 1.5 ml Lesion Material+Trep *phagedenis* (0.75 ml Lesion, 0.75 ml 72 hour cultures of Isolates 189, 190, 191 in MTGE)

Days 8, 11, 15, 19: Moisten wraps with 1.5 ml MTGE/FBS (1.0 MTGE/0.5 mlFBS) Day 22: Remove wraps 3 Control Calves:

Day 1: Abrade all 4 feet of all calves and wrap—soak with sterile rumen fluid/MTGE Days 3, 5, 8, 11, 15, 19: Inoculate
with: Foot 1: MTGE
Foot 2: MTGE
Foot 3: MTGE
Foot 4: MTGE
Day 22:
Remove Wraps Controls: In this study design we basically have two sets of control calves. The first are comprised of the 18 "control feet" on animals with the other feet induced. These controls are exposed to DD lesions in the environment during the study. The other control calves (3 calves or 12 feet) were housed separately from the 18 calves and no attempts were made to inoculate these animals with lesion material. They did however come through the same chute system for pictures etc.

Results:
Protocol 1: 1.5 ml MTGE broth only
Protocol 2: 1.5 ml Lesion Material (Macerated tissue)+Trep phagedenis (0.75 ml Lesion, 0.75 ml 72 hour cultures of Isolates 189, 190, 191 in MTGE)
Protocol 3: 1.5 ml Lesion Material+Dichelobacter (0.75 ml Lesion, 0.75 ml ATCC Dichelobacter culture in MTGE broth) (Dichelobacter culture (48 hr and 120 hr) grown on TAS agar and transferred from agar to broth for inoculation).
Protocol 4: 1.5 ml Lesion Material (0.75 ml Lesion, 0.75 ml MTGE)

All lesions induced were stage 3 (active lesions) on the Iowa DD Lesion Scoring system. In order to further differentiate the lesions during the induction study we developed a lesion severity scoring system that works on a 1-10 scale with 10 being the most severe. The scoring system considers the presence of a skin defect, if the lesion is larger or smaller than initial abrasion, hyperemia of the lesion and if reepithelialization is occurring.

We were successful at getting 100% induction in the Protocol 4 group and 77-83% induction in Protocols 2 and 3. The control calves in the treatment pen (Protocol 1 Treatment pen) had a significant number of lesions although their lesion severity score was lower than that of the induction groups. The control calves in the control pen had a much lower induction rate and lesion severity score.

Example 2

DD Induction Using Frozen and Diluted Inoculum Produced in Bulk

Since preparation of large volumes of macerated inoculum is time and labor intensive, we wanted to evaluate the induction success using frozen or diluted inoculum. As calves from each induction protocol were housed in separate pens, an accurate assessment of the true induction success as compared to the controls without the possibility of within-pen cross-contamination was possible. For this experiment 40 calves representing 160 feet were enrolled and at the time of wrap removal, 148 of the original 160 feet qualified for analysis with no wraps lost and three calves (12 feet) was removed due to antibiotic treatment for respiratory disease.

At the conclusion of the trial, all three tested protocols (macerated-1, frozen-2, and dilute-3) had decidedly higher ($p<0.0001$) lesion scores than the segregated negative controls. All three protocols had greater than 85% induction with average lesion scores higher than 8.5. Of the 28 control feet, there was not a single foot that had a lesion score greater than 0. Although lesion scores and percent induction were slightly higher in the typical macerated lesion protocol (1), there was no statistical difference between the other variations of macerated lesion material in protocols 2 and 3 indicating that a 90% dilution of inoculum or freezing of inoculum did not significantly decrease the effectiveness of the induction. Protocol 1 (standard dose, fresh macerated DD lesion) had the highest lesion scores (9.57) and percent induction (95%) of any protocols tested to date. There was a slight decrease in lesion scores with the frozen and 10% inoculum groups, although it was not found to be statistically significant than protocol 1. This indicates that the amount of inoculum needed to induce DD lesions was far less than originally anticipated.

In this study foot sensitivity was also measured as an outcome of pain associated with lesion formation. The number of sensitive feet remained very low for the first 12 days of the trial with only three sensitive feet the first 2 days after abrasion. Approximately two weeks post abrasion the number of sensitive feet began to increase rapidly with an initial peak at day 19. This was followed by a period of time with lower numbers of sensitive feet until the end of the trial where the number of sensitive feet peaked again at day 26. There was a statistical difference in DD associated lameness between the different protocols ($p<0.05$), with control feet having a significantly lower number of lame feet compared to all induction protocols. There was also no statistical difference in lameness between the three induction protocols. A high level of correlation was also observed between macroscopic score and foot sensitivity ($r(147)=0.23$, $p<0.0001$) with 21% of feet with DD lesions showing signs of sensitivity.

TABLE 3

The Number of Lame Feet for Each of Protocol.

| Groups | n | Lame | Average | Std Err |
|---|---|---|---|---|
| Control | 28 | 0 | 0.0% | 0.000 |
| Frozen | 48 | 6 | 12.5%* | 0.048 |
| Low Dose | 27 | 7 | 25.9%* | 0.086 |
| Treatment | 44 | 11 | 25.0%* | 0.066 |

Lameness was defined as a foot that had a minimum of two observations of sensitivity in which at least one of them was a score of 2 or more. *Indicates statistical significance when compared to controls The histological scoring of biopsies obtained at the time of wrap removal was analyzed for correlation to our macroscopic scoring system. There was a much larger separation of lesion scores with the majority (140/147) of the scores either being 0 indicating normal skin or a lesion score of 9 or 10 indicating a large lesion. The lesion scores were highly correlated ($r(145)=0.87$, $p<0.0001$) to the histopathology scores with 98% of lesion scores 9 or 10 scored as grade 3 and 92% of lesion score 0 scored as Grade 1.

Deposits

A deposit of the macerated tissue culture has been made by Iowa State University with the American Type Culture Collection (ATCC), Manassas, VA 20110 USA, ATCC Deposit No. PTA-124690. Access to these deposits will be available during the pendency of the application to the Commissioner of Patents and Trademarks and persons determined by the Commissioner to be entitled thereto upon request. Upon allowance of any claims in the application, the Applicant(s) will make available to the public without restriction a deposit of each of these cultures with the American Type Culture Collection (ATCC), Manassas, VA 20110 USA. The cells deposited with the ATCC were taken from the same deposit maintained at Iowa State University since prior to the filing date of this application. Additionally, Applicant has met all the requirements of 37 C.F.R. § 1.801-1.809, including providing an indication of the viability of the sample when the deposit was made. This deposit of the aforementioned cell lines will be maintained in the ATCC Depository, which is a public depository, for a period of 30 years, or 5 years after the most recent request, or for the enforceable life of the patent, whichever is longer, and will be replaced if it ever becomes nonviable during that period. Applicant will impose no restrictions on the availability of the deposited material from the ATCC; however, Applicant has no authority to waive any restrictions imposed by law on the transfer of biological material or its transportation in commerce.

What is claimed is:

1. A method of generating an animal model of digital dermatitis comprising:
   abrading one or more feet of an animal subject;
   wrapping said abraded feet,
   inoculating the abraded feet with an inoculum composition comprising a culture of macerated digital dermatitis tissue,
   and thereafter removing the wrap, wherein said treatment results in formation of digital dermatitis lesions in the interdigital space, and does not include a water maceration step.
2. The method of claim 1 wherein said animal is a bovine.
3. The method of claim 2 wherein said bovine is a calf.
4. The method of claim 1 wherein said wrap is soaked in anaerobic media fluid.
5. The method of claim 1 wherein said wrap is soaked in rumen fluid.
6. The method of claim 1 wherein said wrap is removed after 32 days or less.
7. The method of claim 1 wherein said inoculum is frozen.
8. The method of claim 1 wherein said inoculum is diluted.
9. The method of claim 1 wherein said inoculating step further comprises the step of;
   inoculating said abraded feet a second time with said composition prior to removing said wrap.
10. The method of claim 9 wherein said second inoculation is 2 days after said first inoculation.
11. A culture of macerated tissue for inducing digital dermatitis comprising Accession No. PTA-124690.
12. The macerated tissue culture of claim 1 comprising one or more of the following strains: *Treponema*-like, *Porphorymonas, Bacteroides, Dichelobacter nodosus* and *Campylobacter ureolyticus* strains.
13. The method of claim 1 wherein said culture is frozen.
14. The method of claim 1 wherein said culture is diluted.
15. A method for determining the effectiveness of a treatment for digital dermatitis comprising:
    inducing digital dermatitis in an animal subject by:
       abrading one or more feet of an animal subject; wrapping said abraded feet, inoculating the abraded feet with a composition comprising a culture of macerated digital dermatitis tissue, and thereafter removing the wrap, wherein said treatment results in formation of digital dermatitis lesions in the interdigital space,
    treating said animal with a proposed treatment of digital dermatitis, and
    evaluating the animal for amelioration of any symptoms or conditions associated with the disease.
16. A method of preparing a composition comprising at least one immunogenic protein from macerated tissue, said method comprising:
    a) cultivating one or more strains from macerated digital dermatitis tissue anaerobically, wherein one or more strains is chosen from the group consisting of, *Treponema*-like, *Porphorymonas, Bacteroides, Dichelobacter nodosus* and *Campylobacter ureolyticus* strains;
    b) recovering the supernatant from the culture;
    c) isolating at least one immunogenic protein from the supernatant; and
    d) adding a pharmaceutically acceptable carrier.
17. The method of claim 16, further comprising the step of inactivating all of the proteins of said one or more strains of claim 16.
18. An inoculum of digital dermatitis associated pathogens comprising the culture of macerated tissue of claim 11 (ATCC No. PTA-124690) and a carrier.
19. An animal model of digital dermatitis comprising a bovine with a foot abrasion that has been inoculated with the inoculum of claim 18.
20. A method of evaluating a purported agent useful for treating, preventing or ameliorating the symptoms of digital dermatitis comprising:
    administering to an animal in need thereof said agent, wherein said animal is an animal model generated by the method of claim 1 and thereafter
    evaluating the severity, number or size of digital dermatitis lesions.

* * * * *